(12) United States Patent
Kawamura et al.

(10) Patent No.: US 9,000,225 B2
(45) Date of Patent: Apr. 7, 2015

(54) METHOD FOR PRODUCING 2-(ARYLOXYMETHYL) BENZALDEHYDE COMPOUND

(75) Inventors: Mitsunobu Kawamura, Osaka (JP); Masashi Takimoto, Shizuoka (JP); Tomonori Yamaoka, Shizuoka (JP); Yoshio Onogawa, Shizuoka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/128,248

(22) PCT Filed: Jun. 27, 2012

(86) PCT No.: PCT/JP2012/066401
§ 371 (c)(1),
(2), (4) Date: Jan. 31, 2014

(87) PCT Pub. No.: WO2013/002264
PCT Pub. Date: Jan. 3, 2013

(65) Prior Publication Data
US 2014/0213825 A1   Jul. 31, 2014

(30) Foreign Application Priority Data
Jun. 27, 2011  (JP) .................................. 2011-141533

(51) Int. Cl.
C07C 45/64   (2006.01)
C07C 45/43   (2006.01)

(52) U.S. Cl.
CPC ................. *C07C 45/64* (2013.01); *C07C 45/43* (2013.01)

(58) Field of Classification Search
None
See application file for complete search history.

(56) References Cited

U.S. PATENT DOCUMENTS

| | | | |
|---|---|---|---|
| 4,439,620 A | 3/1984 | Klauke et al. | |
| 7,851,659 B2 | 12/2010 | Nakazawa | |
| 7,994,367 B2 | 8/2011 | Nakazawa | |
| 8,258,349 B2 | 9/2012 | Nakazawa | |
| 8,338,625 B2 | 12/2012 | Onogawa et al. | |
| 2010/0210879 A1 | 8/2010 | Nakazawa | |
| 2010/0234645 A1 | 9/2010 | Nakazawa | |
| 2010/0292513 A1 | 11/2010 | Nakazawa | |
| 2011/0098489 A1 | 4/2011 | Onogawa et al. | |

FOREIGN PATENT DOCUMENTS

| | | | |
|---|---|---|---|
| CN | 101939281 A | 1/2011 | |
| EP | 2149545 A1 | 2/2010 | |
| EP | 2241546 A1 | 10/2010 | |
| JP | 09-095462 A | 4/1997 | |
| JP | H11-199536 A | 7/1999 | |
| JP | 2006335737 A | 12/2006 | |
| JP | 2009001554 A | 1/2009 | |
| JP | 2009007334 A | 1/2009 | |
| JP | 2009215286 A | 9/2009 | |
| JP | 2009298746 A | 12/2009 | |
| WO | 2009/101898 A1 | 8/2009 | |

OTHER PUBLICATIONS

Machine translation fro WO-2009/101898 document.*
(Continued)

*Primary Examiner* — Brandon Fetterolf
*Assistant Examiner* — Ana Z Muresan
(74) *Attorney, Agent, or Firm* — Sughrue Mion, PLLC

(57) ABSTRACT

A new process for producing a 2-(aryloxymethyl)benzaldehyde compound and the like are provided. More particularly, a process for producing a 2-(aryloxymethyl)benzaldehyde compound represented by formula (4) comprising step (A) of hydrolyzing a compound represented by the following formula (1); and step (B) of reacting a compound represented by formula (2) obtained in step (A) and a compound represented by formula (3) or a salt thereof is provided;

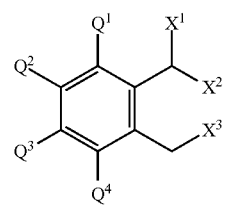

(1)

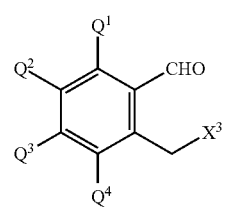

(2)

Ar—OH  (3)

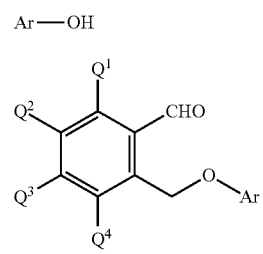

(4)

in formulae, $X^1$, $X^2$ and $X^3$ each represent independently a chlorine atom, a bromine atom or an iodine atom, $Q^1$, $Q^2$, $Q^3$ and $Q^4$ each represent independently a hydrogen atom or a halogen atom, and Ar represents a phenyl group optionally having a substituent).

6 Claims, No Drawings

(56) References Cited

OTHER PUBLICATIONS

Litwinienko et al. Themochimica Acta. 1997, 307, 97-106.*
Sigma-Aldrich catalog (product 339741).*
International Preliminary Report on Patentability and Written Opinion issued Jan. 7, 2014 in International Application No. PCT/JP2012/066401.
Jikken Kagaku Koza 21 Yuki Gosei III, —Aldehyde, Ketone, Quinone—, 4th Edition, 1991, p. 28, with partial English translation.
Lewis, Richard J., Sr., "Hawley's Condensed Chemical Dictionary," Twelfth Edition, p. 31, 1993.
State Intellectual Property Office of People's Republic of China, "First Office Action," issued in connection with Chinese Patent Application No. 201280031571.0, dated Sep. 24, 2014.
European Patent Office, "Communication with Extended European Search Report," issued in connection with European Patent No. 12804734.7, dated Jan. 8, 2015.
Japanese Patent Office, "Office Action," issued in connection with Japanese Patent Application No. 2011-141533, dated Jan. 6, 2015.

* cited by examiner

METHOD FOR PRODUCING 2-(ARYLOXYMETHYL) BENZALDEHYDE COMPOUND

CROSS REFERENCE TO RELATED APPLICATIONS

This application is a National Stage of International Application No. PCT/JP2012/066401 filed Jun. 27, 2012, claiming priority based on Japanese Patent Application No. 2011-141533 filed Jun. 27, 2011, the contents of all of which are incorporated herein by reference in their entirety.

TECHNICAL FIELD

The present invention relates to a process for producing a 2-(aryloxymethyl)benzaldehyde compound and the like.

BACKGROUND ART

A 2-(aryloxymethyl)benzaldehyde compound such as 2-(2,5-dimethylphenoxymethyl)benzaldehyde is useful, for example, as an intermediate for producing agricultural germicides (for example, see JP 9-95462 A).

As a process for producing a 2-(aryloxymethyl)benzaldehyde compound, for example, in JP 2009-215286 A, a method for obtaining 2-(2,5-dimethylphenoxymethyl)benzaldehyde by reacting 2,5-dimethylphenol and 2-(chloromethyl)benzal chloride, reacting the resulting 2-(2,5-dimethylphenoxymethyl)benzal chloride and sodium methoxide to obtain dimethyl acetal, and mixing this dimethyl acetal with an aqueous sulfuric acid solution is described. In addition, in JP 2009-298746 A, a method for obtaining 2-(2,5-dimethylphenoxymethyl)benzaldehyde by reacting 2,5-dimethylphenol and 2-(chloromethyl)benzal chloride, reacting the resulting 2-(2,5-dimethylphenoxymethyl)benzal chloride and ethylene glycol in the presence of calcium carbonate to obtain cyclic acetal, and mixing this cyclic acetal with concentrated hydrochloric acid is described.

An object of the present invention is to provide a new process for producing a 2-(aryloxymethyl)benzaldehyde compound and the like.

SUMMARY OF INVENTION

The present inventors intensively studied, and reached the present invention.

That is, the present invention is as follows:

[1] A process for producing a 2-(aryloxymethyl)benzaldehyde compound represented by formula (4):

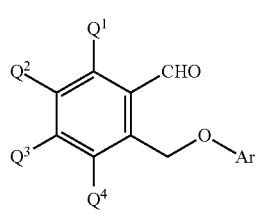

(4)

wherein $Q^1$, $Q^2$, $Q^3$ and $Q^4$ each represent independently a hydrogen atom or a halogen atom, and Ar represents a phenyl group optionally having a substituent,
the process comprising step (A) of hydrolyzing a compound represented by formula (1):

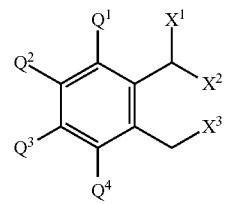

(1)

wherein $X^1$, $X^2$ and $X^3$ each represent independently a chlorine atom, a bromine atom or an iodine atom, $Q^1$ and $Q^2$, $Q^3$ and $Q^4$ are each as described above;
and
step (B) of reacting a compound represented by formula (2):

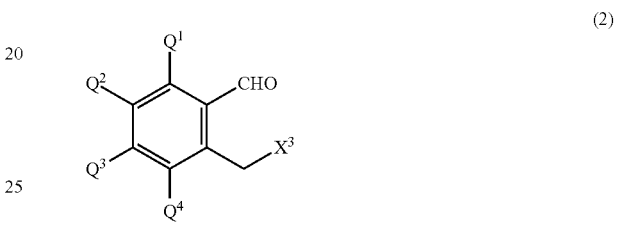

(2)

wherein $X^3$, $Q^1$, $Q^2$, $Q^3$, and $Q^4$ are each as described above, obtained in step (A), and a compound represented by formula (3):

Ar—OH   (3)

wherein Ar is as described above;
or a salt thereof.

[2] The process according to [1], wherein step (A) is a step of hydrolyzing the compound represented by formula (1) in the presence of sulfuric acid.

[3] The process according to [1], wherein step (A) is performed by mixing the compound represented by formula (1) and sulfuric acid having a concentration of 84.5% by weight or more, and further mixing the resulting mixture and water.

[4] The process according to any one of [1] to [3], wherein before step (B) is performed, the compound represented by formula (2) obtained in step (A) is neutralized.

[5] The process according to any one of [1] to [4], wherein before step (B) is performed, the compound represented by formula (2) obtained in step (A), and at least one selected from the group consisting of a polymerization inhibitor and an antioxidant are mixed.

[6] The process according to any one of [1] to [5], wherein step (B) is a step of reacting the compound represented by formula (2) obtained in step (A), and the compound represented by formula (3) or a salt thereof in the presence of a phase transfer catalyst.

According to the present invention, a new process for producing a 2-(aryloxymethyl)benzaldehyde compound and the like can be provided.

DESCRIPTION OF EMBODIMENT

The present invention will be explained in detail below.

In formulae (1), (2) and (4), $Q^1$, $Q^2$, $Q^3$ and $Q^4$ each represent independently a hydrogen atom or a halogen atom. Examples of the halogen atom represented by $Q^1$, $Q^2$, $Q^3$ and $Q^4$ include a fluorine atom, a chlorine atom, a bromine atom and an iodine atom. $Q^1$, $Q^2$, $Q^3$ and $Q^4$ are preferably a hydrogen atom.

In formula (1), $X^1$, $X^2$ and $X^3$ each represent independently a chlorine atom, a bromine atom or an iodine atom. $X^1$ and $X^2$ are preferably the same atom, and $X^1$, $X^2$ and $X^3$ are preferably all a chlorine atom, from the viewpoint of economical efficiency. In formula (2), $X^3$ represents a chlorine atom, a bromine atom or an iodine atom, preferably a chlorine atom.

In formulae (3) and (4), Ar represents a phenyl group optionally having a substituent.

Examples of the substituent possessed by the phenyl group include preferably an alkyl group having 1 to 4 carbon atoms such as a methyl group, an ethyl group, a propyl group, an isopropyl group, a butyl group, an isobutyl group and a tert-butyl group; a halogen atom such as a fluorine atom and a chlorine atom. When the phenyl group has a substituent, the number of the substituent is not limited, but is preferably 1 to 3, more preferably 1 or 2, and further preferably 2.

Examples of the phenyl group optionally having a substituent include, for example, a phenyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,4,6-trimethylphenyl group, a 2-ethylphenyl group, a 3-ethylphenyl group, a 4-ethylphenyl group, a 2,3-diethylphenyl group, a 2,4-diethylphenyl group, a 2,5-diethylphenyl group, a 2,6-diethylphenyl group, a 3,5-diethylphenyl group, a 2,4,6-triethylphenyl group, a 2-(n-propyl)phenyl group, a 3-(n-propyl)phenyl group, a 4-(n-propyl)phenyl group, a 2,4-di(n-propyl)phenyl group, a 2,5-di(n-propyl)phenyl group, a 2,6-di(n-propyl)phenyl group, a 2,4,6-tri(n-propyl)phenyl group, a 2-isopropylphenyl group, a 3-isopropylphenyl group, a 4-isopropylphenyl group, a 2,4-diisopropylphenyl group, a 2,5-diisopropylphenyl group, a 2,6-diisopropylphenyl group, a 2,4,6-triisopropylphenyl group, a 2-(n-butyl)phenyl group, a 3-(n-butyl)phenyl group, a 4-(n-butyl)phenyl group, a 2,4-di(n-butyl)phenyl group, a 2,5-di(n-butyl)phenyl group, a 2,6-di(n-butyl)phenyl group, a 2,4,6-tri(n-butyl)phenyl group, a 2-isobutylphenyl group, a 3-isobutylphenyl group, a 4-isobutylphenyl group, a 2,4-diisobutylphenyl group, a 2,5-diisobutylphenyl group, a 2,6-diisobutylphenyl group, a 2,4,6-triisobutylphenyl group, a 2-(tert-butyl)phenyl group, a 3-(tert-butyl)phenyl group, a 4-(tert-butyl)phenyl group, a 2,5-di-(tert-butyl)phenyl group, a 2,4-di-(tert-butyl)phenyl group, a 2,6-di-(tert-butyl)phenyl group, a 2,4,6-tri-(tert-butyl)phenyl group, a 2-fluorophenyl group, a 4-fluorophenyl group, a 2,4-difluorophenyl group, a 2,4,6-trifluorophenyl group, a pentafluorophenyl group, a 2-chlorophenyl group, a 4-chlorophenyl group, a 2,4-dichlorophenyl group, a 2,4,6-trichlorophenyl group and a pentachlorophenyl group.

The phenyl group optionally having a substituent represented by Ar is preferably a phenyl group, a 2-methylphenyl group or a 2,5-dimethylphenyl group, more preferably a 2-methylphenyl group or a 2,5-dimethylphenyl group, and further preferably a 2,5-dimethylphenyl group.

The present invention comprises step (A) of hydrolyzing a compound represented by formula (1) (hereinafter, referred to as "compound (1)" in some cases), and step (B) of reacting a compound represented by formula (2) obtained in step (A) (hereinafter, referred to as "compound (2)" in some cases), and a compound represented by formula (3) or a salt thereof (hereinafter, referred to as "compound (3)" in some cases). By performing step (A) and step (B), a 2-(aryloxymethyl)benzaldehyde compound represented by formula (4) (hereinafter, referred to as "compound (4)" in some cases) is produced.

First, step (A) will be explained.

Examples of the compound (1) used in step (A) include, for example, 2-(chloromethyl)benzal chloride, 2-(bromomethyl)benzal chloride, 2-(iodomethyl)benzal chloride, 2-(chloromethyl)-3-chlorobenzal chloride, 2-(bromomethyl)-3-chlorobenzal chloride, 2-(iodomethyl)-3-chlorobenzal chloride, 2-(chloromethyl)-4-chlorobenzal chloride, 2-(bromomethyl)-4-chlorobenzal chloride, 2-(iodomethyl)-4-chlorobenzal chloride, 2-(chloromethyl)-5-chlorobenzal chloride, 2-(bromomethyl)-5-chlorobenzal chloride, 2-(iodomethyl)-5-chlorobenzal chloride, 2-(chloromethyl)-6-chlorobenzal chloride, 2-(bromomethyl)-6-chlorobenzal chloride, 2-(iodomethyl)-6-chlorobenzal chloride, 2-(chloromethyl)-4-bromobenzal chloride, 2-(bromomethyl)-4-bromobenzal chloride, 2-(iodomethyl)-4-bromobenzal chloride, 2-(chloromethyl)-4-iodobenzal chloride, 2-(bromomethyl)-4-iodobenzal chloride, 2-(iodomethyl)-4-iodobenzal chloride, 2-(chloromethyl)benzal bromide, 2-(bromomethyl)benzal bromide, 2-(iodomethyl)benzal bromide, 2-(chloromethyl)-3-chlorobenzal bromide, 2-(bromomethyl)-3-chlorobenzal bromide, 2-(iodomethyl)-3-chlorobenzal bromide, 2-(chloromethyl)-4-chlorobenzal bromide, 2-(bromomethyl)-4-chlorobenzal bromide, 2-(iodomethyl)-4-chlorobenzal bromide, 2-(chloromethyl)-5-chlorobenzal bromide, 2-(bromomethyl)-5-chlorobenzal bromide, 2-(iodomethyl)-5-chlorobenzal bromide, 2-(chloromethyl)-6-chlorobenzal bromide, 2-(bromomethyl)-6-chlorobenzal bromide, 2-(iodomethyl)-6-chlorobenzal bromide, 2-(chloromethyl)-4-bromobenzal bromide, 2-(bromomethyl)-4-bromobenzal bromide, 2-(iodomethyl)-4-bromobenzal bromide, 2-(chloromethyl)-4-iodobenzal bromide, 2-(bromomethyl)-4-iodobenzal bromide, 2-(iodomethyl)-4-iodobenzal bromide, 2-(chloromethyl)benzal iodide, 2-(bromomethyl)benzal iodide, 2-(iodomethyl)benzal iodide, 2-(chloromethyl)-3-chlorobenzal iodide, 2-(bromomethyl)-3-chlorobenzal iodide, 2-(iodomethyl)-3-chlorobenzal iodide, 2-(chloromethyl)-4-chlorobenzal iodide, 2-(bromomethyl)-4-chlorobenzal iodide, 2-(iodomethyl)-4-chlorobenzal iodide, 2-(chloromethyl)-5-chlorobenzal iodide, 2-(bromomethyl)-5-chlorobenzal iodide, 2-(iodomethyl)-5-chlorobenzal iodide, 2-(chloromethyl)-6-chlorobenzal iodide, 2-(bromomethyl)-6-chlorobenzal iodide, 2-(iodomethyl)-6-chlorobenzal iodide, 2-(chloromethyl)-4-bromobenzal iodide, 2-(bromomethyl)-4-bromobenzal iodide, 2-(iodomethyl)-4-bromobenzal iodide, 2-(chloromethyl)-4-iodobenzal iodide, 2-(bromomethyl)-4-iodobenzal iodide, and 2-(iodomethyl)-4-iodobenzal iodide.

The compound (1) is preferably 2-(chloromethyl)benzal chloride, 2-(chloromethyl)benzal bromide, 2-(bromomethyl)benzal chloride or 2-(bromomethyl)benzal bromide, and more preferably 2-(chloromethy)benzal chloride.

The compound (1) may be a compound which is commercially available, for example, a compound produced according to the method described in JP 2006-335737 A or the like.

Hydrolysis is performed in the presence of an organic solvent or in the absence of an organic solvent, and is performed preferably in the absence of an organic solvent.

Step (A) is performed preferably in the presence of sulfuric acid, specifically, for example, is performed by mixing the compound (1) and 84.5% by weight or more of sulfuric acid, and further mixing the resulting mixture and water. In the present invention, mixing of the compound (1) and sulfuric acid having a concentration of 84.5% by weight or more is referred to as "step A-1" in some cases. In addition, further mixing of the mixture obtained via step (A-1) and water is referred to as "step A-2" in some cases. In the present invention, "water" means that water and an aqueous medium (an aqueous solution in which a substance soluble in water is dissolved in water) are included, unless otherwise noted.

A concentration of sulfuric acid used in step (A-1) is more preferably 85% by weight or more and 96% by weight or less, and further preferably 90% by weight or more and 96% by weight or less. An amount of sulfuric acid is preferably 1 mol or more, and more preferably 2 mol or more based on 1 mol of the compound (1). There is no upper limit of an amount of sulfuric acid, but 4 mol or less based on 1 mol of the compound (1) is practical. When an amount of sulfuric acid is 1 mol or more based on 1 mol of the compound (1), this is preferable in that a reaction between the compound (1) and sulfuric acid progresses smoothly.

The reaction temperature in step (A-1) is not particularly limited, but at the temperature of 15° C. or higher, the reaction rate is sufficiently maintained, and this is preferable. This reaction temperature is preferably 25° C. or lower in respect of stability of the compound (2) produced. There is particularly no limitation of the reaction time, but in view of the practical range in industrial production, 15 hours or shorter is preferable, and 8 hours or shorter is more preferable. There is particularly no lower limit, but 3 hours or longer is practical.

A method of carrying out step (A-1) is not limited, but preferably is performed by a method of adding dropwise preferably into sulfuric acid having the aforementioned concentration. In addition, since an induction phase is seen in a reaction initial stage, a method of adding dropwise a part of the compound (1), confirming that a reaction between the compound (1) and sulfuric acid having a concentration of 84.5% by weight or more is initiated, and adding the remaining compound (1) can be also adopted.

In the present aspect, even when sulfuric acid used in step (A-1) contains water at less than 1 mol based on 1 mol of the compound (1), a hydrolysis reaction can be completed by further mixing a mixture obtained via step (A-1) and water. That is, the hydrolysis reaction may progress in step (A-1), or may be completed via step (A-2). Sulfuric acid used in step (A-1) preferably contains water at 0.4 mol or more, more preferably contains water at 0.8 mol or more, and further preferably contains water at 1 mol or more based on 1 mol of the compound (1). There is particularly no upper limit of an amount of water contained in sulfuric acid, but 2 mol or less based on 1 mol of the compound (1) is practical.

The mixture obtained in step (A-1) is present in a state where the mixture is uniformly mixed in a reaction liquid, and by performing step (A-2) of further mixing the mixture and water, the compound (2) can be obtained, and by recovering an organic compound component containing the compound (2) as an organic layer, the organic compound component, and water and the aqueous layer containing components dissolved therein can be separated. Herein, in the organic compound component, the compound (1) which is a raw material compound and the compound (2) which is a product are present together, in some cases. Since separation of both organic compound components is usually not easy, and the compound (2) is an easily degradable compound, it is not practical to perform purification treatment by heating or the like. In other words, it is important to produce the compound (2) at a high yield at a stage of a reaction of producing the compound (2).

It is preferable to add an amount of water used in step (A-2) so that a concentration of sulfuric acid in the mixture obtained via step (A-2) becomes 70% by weight or less, in that liquid separation of the resulting organic layer and the aqueous layer is performed good, and the compound (2) is separated. There is no upper limit of a use amount of water, but use of more water than necessary becomes disadvantageous in economical efficiency. The temperature at which water is added, in view of stability of the compound (2), is preferably 30° C. or lower, and in view of a solidification point of water, the temperature which is lower in the range of 5° C. or higher and 30° C. or lower is further preferable. When the organic layer and the aqueous layer are liquid-separated, the temperature is preferably in the range of 15° C. to 30° C. in respect of liquid separability.

Upon isolation and/or purification of the compound (2), in order to improve separability from water, an organic solvent which is immiscible with water can be used. Examples of such organic solvent include aromatic solvents such as xylene, toluene and benzene; aliphatic hydrocarbon solvents such as pentane, hexane, heptane and cyclohexane. These organic solvents may be alone, or a mixture of two or more kinds. The organic solvent is preferably an aromatic solvent, and more preferably xylene or toluene. A use amount of the organic solvent is not particularly limited, but from the viewpoint of economical efficiency, a use amount is, for example, 20 parts by weight or less based on 1 part by weight of the compound (2). When the organic solvent is used upon isolation and/or purification of the compound (2), the compound (2) is obtained as a solution of the organic solvent. Such solution of the organic solvent may be subjected to concentration treatment, if necessary.

The compound (2) contained in the recovered organic layer can provide the compound (2) having a high yield and a high concentration to step (B). In the present aspect, it is preferable that a concentration of the compound (2) $[\_\eta_{compound\ (2)}]$, that is a ratio of a molar quantity of the compound (2) $[M_{compound\ (2)}]$ relative to a total amount of a molar quantity of the compound (1) $[M_{compound\ (1)}]$ and a molar quantity of the compound (2) $[M_{compound\ (2)}]$, $[\eta_{compound\ (2)} = [M_{compound\ (2)}]/[M_{compound\ (2)}]+[M_{compound\ (1)}])$ is increased. A concentration of the compound (2) $[\eta_{compound\ (2)}]$ is preferably 95% or more, and more preferably 98% or more. There is particularly no upper limit, but for example, in view of extension of the reaction time of step (A), it is also possible to define the upper limit as 100% or less. Like this, by obtaining the compound (2) having a high concentration, a raw material of good quality in which an amount of the compound (1) is suppressed small is obtained.

The compound (2) obtained in step (A) is preferably neutralized before step (B) is performed. Neutralization is performed by mixing the compound (2) or a mixture containing the compound (2) and an aqueous alkaline solution (preferably, an aqueous solution containing an alkali buffer). Thereupon, it is preferable to measure a pH of the compound (2) or a mixture containing the compound (2) and adjust a pH to 6 to 8. The kind of the alkali used in neutralization is not limited, but it is preferable to use alkaline pH adjusting agents having the buffering effect such as disodium hydrogen phosphate. In addition, in the present invention, a pH refers to a value measured by the method shown in Examples, unless otherwise noted.

Further, before step (B) is performed, preferably, the compound (2) obtained in step (A), and at least one selected from the group consisting of a polymerization inhibitor and an antioxidant (hereinafter, referred to as stabilizer in some cases) are mixed. Examples of the stabilizer include 2,6-bis(1,1-dimethylethyl)-4-methylphenol (hereinafter, referred to as BHT in some cases), hydroquinone, monomethyl hydroquinone, phenothiazine, methanol, Quino Power (registered trademark), $MnCl_2$, $CuCl_2$ and TEMPO, and at least one selected from the group consisting of 2,6-bis(1,1-dimethylethyl)-4-methylphenol (BHT), hydroquinone, monomethyl hydroquinone and phenothiazine is preferable, phenothiazine and BHT are more preferable, and BHT is further preferable. A use amount of the stabilizer is preferably 50 to 500 ppm (stabilizer/compound (2)), and more preferably 100 to 200 ppm on the weight basis relative to the compound (2). When a use amount is less than 50 ppm, or when a use amount is more than 500 ppm, stability of the compound (2) is not improved as compared with stability of the compound (2) not mixed with the stabilizer, in some cases.

Examples of the thus obtained compound (2) include 2-(chloromethyl)benzaldehyde, 2-(bromomethyl)benzaldehyde, 2-(iodomethyl)benzaldehyde, 2-(chloromethyl)-3-chlorobenzaldehyde, 2-(bromomethyl)-3-chlorobenzaldehyde, 2-(iodomethyl)-3-chlorobenzaldehyde, 2-(chloromethyl)-4-chlorobenzaldehyde, 2-(bromomethyl)-4-chlorobenzaldehyde, 2-(iodomethyl)-4-chlorobenzaldehyde, 2-(chloromethyl)-5-chlorobenzaldehyde, 2-(bromomethyl)-5-chlorobenzaldehyde, 2-(iodomethyl)-5-chlorobenzaldehyde, 2-(chloromethyl)-6-chlorobenzaldehyde, 2-(bromomethyl)-6-chlorobenzaldehyde, 2-(iodomethyl)-6-chlorobenzaldehyde, 2-(chloromethyl)-4-bromobenzaldehyde, 2-(bromomethyl)-4-bromobenzaldehyde, 2-(iodomethyl)-4-bromobenzaldehyde, 2-(chloromethyl)-4-iodobenzaldehyde, 2-(bromomethyl)-4-iodobenzaldehyde, and 2-(iodomethyl)-4-iodobenzaldehyde. Among them, 2-(chloromethyl)benzaldehyde or 2-(bromomethyl)benzaldehyde is preferable, and 2-(chloromethyl)benzaldehyde is more preferable.

Then, step (B) will be explained.

Examples of the compound (3) used in step (B) include phenol, 2-methylphenol, 2-ethylphenol, 2-isopropylphenol, 2-t-butylphenol, 3-methylphenol, 4-methylphenol, 4-ethylphenol, 4-isopropylphenol, 4-t-butylphenol, 2,4-dimethylphenol, 2,4-diethylphenol, 2,5-dimethylphenol, 2,5-diethylphenol, 2,5-diisopropylphenol, 2,6-dimethylphenol, 2,6-diethylphenol, 2,6-diisopropylphenol, 3,5-dimethylphenol, 2,4,5-trimethylphenol, 2,4,6-trimethylphenol, 3,4,5-trimethylphenol, 2-chlorophenol, 4-chlorophenol, 2-fluorophenol, 4-fluorophenol, 2,4-difluorophenol, and 2,4,6-trifluorophenol. The compound (3) is preferably 2-methylphenol or 2,5-dimethylphenol, and more preferably 2,5-dimethylphenol.

The compound (3) may be a compound which is commercially available, or may be a compound produced by the known method described, for example, in J. Am. Chem. Soc., 128, 10694 (2006), Tetrahedron Letters, 30, 5215(1989), JP 2002-3426 A or the like.

Examples of the salt of the compound (3) include alkali metal salts of the compound (3) such as a lithium salt of the compound (3), a sodium salt of the compound (3) and a potassium salt of the compound (3); alkaline earth metal salts of the compound (3) such as a calcium salt of the compound (3). The salt of the compound (3) is preferably an alkali metal salt of the compound (3), and more preferably a sodium salt of the compound (3). The salt of the compound (3) may be a salt prepared by mixing the compound (3) and a base descried later.

A use amount of the compound (3) or a salt thereof is, for example, in the range of 0.1 mol to 10 mol, and preferably in the range of 1 mol to 3 mol based on 1 mol of the compound (2).

Step (B) is performed in the presence of a base or in the absence of a base. When the compound (2) and the compound (3) are reacted, step (B) is performed preferably in the presence of a base, and when the compound (2) and a salt of the compound (3) are reacted, the reaction may be performed in the presence of a base, or may be performed in the absence of a base.

Examples of the base used in step (B) include tertiary amines such as trimethylamine, triethylamine and diisopropylethylamine; metal alkoxides such as sodium methoxide, sodium ethoxide and potassium tert-butoxide; alkali metal hydroxides such as lithium hydroxide, sodium hydroxide and potassium hydroxide; alkaline earth metal hydroxides such as calcium hydroxide; alkali metal hydride compounds such as sodium hydride, potassium hydride and lithium hydride; alkaline earth metal hydrides such as calcium hydride; alkali metal carbonate compounds such as sodium carbonate, potassium carbonate and lithium carbonate; alkaline earth metal carbonate compounds such as calcium carbonate; and alkali metal bicarbonate compounds such as sodium bicarbonate, potassium bicarbonate and lithium bicarbonate. The base is preferably alkali metal hydroxide, and more preferably sodium hydroxide. As such base, a base which is commercially available may be used as it is, or the base may be a base mixed with water or a solvent described later.

When the compound (2) and the compound (3) are reacted, a use amount of the base is, for example, in the range of 0.5 mol to 10 mol, and preferably in the range of 0.8 mol to 3 mol based on 1 mol of the compound (3). When a salt of the compound (3) is prepared by mixing the compound (3) and a base, a use amount of the base is, for example, in the range of 0.5 mol to 10 mol, and preferably in the range of 0.8 mol to 3 mol based on 1 mol of the compound (3).

Step (B) is performed under any condition in the presence of a solvent and in the absence of a solvent. Examples of such solvent include aromatic solvents such as xylene, toluene and benzene, and aliphatic hydrocarbon solvents such as pentane, hexane, heptane and cyclohexane.

These solvents may be alone, or may be a mixture of two or more kinds. The solvent is preferably an aromatic solvent, and more preferably xylene or toluene. A use amount of the solvent is not particularly limited, but from the viewpoint of economical efficiency, the amount is, for example, 100 parts by weight or less based on 1 part by weight of the compound (2).

Step (B) is carried out preferably in the presence of a phase transfer catalyst. Examples of such phase transfer catalyst include quaternary ammonium salts such as tetra-n-butylammonium bromide, benzyltriethylammonium chloride, tetra-n-butylammonium hydrogen sulfate, tributylmethylammonium chloride (Aliquat (registered trademark) 175) and trioctylmethylammonium chloride (Aliquat (registered trademark) 336); phosphonium salts such as methyltriphenylphosphonium bromide and tetraphenylphosphonium bromide; and polyether compounds such as 18-crown-6 and polyethylene glycol. The phase transfer catalyst is preferably a quaternary ammonium salt, and more preferably tributylmethylammonium chloride (Aliquat (registered trademark) 175) or tetra-n-butylammonium bromide. A use amount of the phase transfer catalyst is, for example, 0.10 mol or more, and preferably in the range of 0.05 mol to 1 mol based on 1 mol of the compound (2).

Step (B) is performed, for example, by a method of mixing the compound (2), the compound (3) and the base and, if necessary, the phase transfer catalyst, or is performed, for example, by a method of mixing the compound (2) and the salt of the compound (3) and, optionally, the phase transfer catalyst, or is performed, for example, by a method of mixing the compound (3) and the base, and adding the resulting mixture to a mixture of the compound (2) and the phase transfer catalyst. Preferably, step (B) is performed by a method of mixing the compound (3) and the base, and adding the resulting mixture to a mixture of the compound (2) and the phase transfer catalyst.

Step (B) may be also performed in the presence of an iodine compound in that a reaction of the compound (2) and the compound (3) or a salt thereof progresses smoothly. Examples of such an iodine compound include alkali metal iodides such as potassium iodide, sodium iodide and lithium iodide, and iodine. The iodine compound is preferably alkali metal iodide, and more preferably potassium iodide. The iodine compound may be, for example, an iodine compound which is commercially available, or may be an iodine compound produced by the arbitrary known method. A use amount of the iodide compound is, for example, 0.01 mol or more, and preferably in the range of 0.05 mol to 1 mol based on 1 mol of the compound (2).

The reaction temperature in step (B) is selected, for example, from the range of −5° C. or higher and a boiling point of the solvent or lower, preferably the range of 10° C. to 100° C. The reaction time is different depending on the reaction temperature or the like, and is, for example, in the range of 1 to 15 hours. Step (B) may be performed under an atmospheric pressure, or may be under pressure. In the method of mixing the compound (3) and the base, and adding the resulting mixture to a mixture of the compound (2) and the phase transfer catalyst, mixing of the compound (3) and the base is performed at the temperature selected from the temperature of −5° C. or higher and a boiling point of the solvent or lower, and preferably is performed at the temperature selected from the range of 10° C. to 100° C. In this case, the time for mixing the compound (3) and the base is different depending on the temperature or the like, and is, for example, in the range of 1 hour to 15 hours.

The degree of progression of a reaction can be confirmed by the analysis means such as gas chromatography, high-performance liquid chromatography, thin layer chromatography and NMR.

The resulting compound (4) is preferably adjusted to a pH of 6 to 8 by contact with water, or a pH adjusting liquid. By adjusting to a pH of 6 to 8, preservation stability of the compound (4) is improved.

The pH adjusting liquid is prepared, for example, from at least one selected from the group consisting of sodium dihydrogen phosphate, disodium hydrogen phosphate, citric acid, boric acid and acetic acid, and water, and is preferably an aqueous solution of sodium dihydrogen phosphate or citric acid.

The compound (4) can be recovered by adjusting the compound (4) to a pH of 6 to 8 by contacting the compound (4) obtained in step (B) with water or a pH adjusting liquid and, thereafter, subjecting the resulting mixture, for example, to liquid separation treatment. In order to improve separability between the compound (4) and water at such liquid separation treatment, the solvent used in step (B) may be appropriately added, and the compound (4) can be also recovered as a solvent. The recovered compound (4) can be also further purified by the purification means such as recrystallization, distillation and column chromatography.

Examples of the compound (4) include 2-(phenoxymethyl)benzaldehyde, 2-(2-methylphenoxymethyl)benzaldehyde, 2-(3-methylphenoxymethyl)benzaldehyde, 2-(4-methylphenoxymethyl)benzaldehyde, 2-(2-ethylphenoxymethyl)benzaldehyde, 2-(4-ethylphenoxymethyl)benzaldehyde, 2-(2-isopropylphenoxymethyl)benzaldehyde, 2-(4-isopropylphenoxymethyl)benzaldehyde, 2-(2-t-butylphenoxymethyl)benzaldehyde, 2-(4-t-butylphenoxymethyl)benzaldehyde, 2-(2,4-dimethylphenoxymethyl)benzaldehyde, 2-(2,5-dimethylphenoxymethyl)benzaldehyde, 2-(2,6-dimethylphenoxymethyl)benzaldehyde, 2-(3,5-dimethylphenoxymethyl)benzaldehyde, 2-(2,4-diethylphenoxymethyl)benzaldehyde, 2-(2,5-diethylphenoxymethyl)benzaldehyde, 2-(2,6-diethylphenoxymethyl)benzaldehyde, 2-(2,5-diisopropylphenoxymethyl)benzaldehyde, 2-(2,6-diisopropylphenoxymethyl)benzaldehyde, 2-(2,4,5-trimethylphenoxymethyl)benzaldehyde, 2-(2,4,6-trimethylphenoxymethyl)benzaldehyde, 2-(3,4,5-trimethylphenoxymethyl)benzaldehyde, 2-(2,5-dimethylphenoxymethyl)-3-chlorobenzaldehyde, 2-(2-methylphenoxymethyl)-3-chlorobenzaldehyde, 2-(2,5-dimethylphenoxymethyl)-4-chlorobenzaldehyde, 2-(2-methylphenoxymethyl)-4-chlorobenzaldehyde, 2-(2,5-dimethylphenoxymethyl)-5-chlorobenzaldehyde, 2-(2-methylphenoxymethyl)-5-chlorobenzaldehyde, 2-(2,5-dimethylphenoxymethyl)-6-chlorobenzaldehyde, 2-(2-methylphenoxymethyl)-6-chlorobenzaldehyde, 2-(2,5-diethylphenoxymethyl)-4-chlorobenzaldehyde, 2-(2-ethylphenoxymethyl)-4-chlorobenzaldehyde, 2-(2,5-diisopropylphenoxymethyl)-4-chlorobenzaldehyde, 2-(2-isopropylphenoxymethyl)-4-chlorobenzaldehyde, 2-(2,5-dimethylphenoxymethyl)-4-bromobenzaldehyde, 2-(2-methylphenoxymethyl)-4-bromobenzaldehyde, 2-(2,5-dimethylphenoxymethyl)-4-iodobenzaldehyde and 2-(2-methylphenoxymethyl)-4-iodobenzaldehyde.

The compound (4) is preferably 2-(2-methylphonxymethyl)benzaldehyde or 2-(2,5-dimethylphenoxymethyl)benzaldehyde, and more preferably 2-(2,5-dimethylphenoxymethyl)benzaldehyde.

EXAMPLES

The present invention will be explained in more detail below by way of examples.

Example 1

A 500 mL flask was charged with 146.1 g (1.43 mol) of sulfuric acid having a concentration of 96% by weight and 9.9 g (0.55 mol) of water, and the resulting mixture was cooled to 25° C. Thereto was added dropwise 115.2 g (0.55 mol) of 2-chloromethylbenzal chloride, and the mixture was stirred at 25° C. for 5 hours. To the resulting mixture was added dropwise 48.3 g of water at the temperature of 30° C. or lower, and then liquid separation treatment was performed. The resulting oily layer was washed with 85.0 g of water and liquid separation-treated to obtain 83.7 g of an oily product containing 2-chloromethylbenzaldehyde as a main component. When the oily product was analyzed by a high-performance liquid chromatography absolute calibration method, a content of 2-chloromethylbenzaldehyde was 88.7% by weight. Yield: 87.3% (based on 2-chloromethylbenzaldehyde).

Further, the oily product was mixed with 83.7 g of a 10 wt % aqueous disodium hydrogen phosphate solution, the resulting mixture was adjusted to a pH of 6 to 8, and liquid separation-treated, and 0.008 g of 2,6-bis(1,1-dimethylethyl)-4-methylphenol (BHT) (100 ppm relative to the oily product containing 2-chloromethylbenzaldehyde as a main component) was added.

A 500 mL flask was charged with 63.8 g (0.52 mol) of 2,5-dimethylphenol and 110.0 g (0.55 mol) of a 20 wt % aqueous sodium hydroxide solution, the temperature of the resulting mixture was elevated to 60° C., and the mixture was stirred at the same temperature for 3 hours. In the 500 mL flask, 8.9 g (0.03 mol) of tetrabutylammonium bromide and 83.7 g (0.47 mol) of the oily product containing 2-chloromethylbenzaldehyde as a main component were mixed, and a mixture prepared from the 2,5-dimethylphenol and the 20 wt % aqueous sodium hydroxide solution was added dropwise for 3 hours while the temperature was retained at 60° C. After completion of addition, the resulting mixture was stirred at the same temperature for 2 hours. The resulting reaction mixture was liquid separation-treated at 60° C., and 130.0 g of a 10 wt % aqueous sodium dihydrogen phosphate solution was mixed into the oily layer. The resulting mixture was adjusted to a pH of 6 to 7, and liquid separation-treated to obtain 135.6 g of an oily product containing 2-(2,5-dimethylphenoxymethyl)benzaldehyde as a main component. When the oily product was analyzed by a high-performance liquid chromatography internal standard method, the content of 2-(2,5-dimethylphenoxymethyl)benzaldehyde was 78.5% by weight.

Yield: 80.6% (based on 2-chloromethylbenzal halide)

A 500 mL flask was charged with 146.1 g (1.43 mol) of sulfuric acid having a concentration of 96% by weight and 9.9 g (0.55 mol) of water, and the resulting mixture was cooled to 25° C. Thereto was added dropwise 115.2 g (0.55 mol) of 2-chloromethylbenzal chloride, and the mixture was stirred at 25° C. for 5 hours. To the resulting mixture was added dropwise 48.3 g of water at the temperature of 30° C. or lower, and then liquid separation treatment was performed. The resulting oily layer was washed with 85.0 g of water and liquid separation-treated to obtain 83.7 g of an oily product containing 2-chloromethylbenzaldehyde as a main component. When the oily product was analyzed by a high-performance liquid chromatography absolute calibration method, a content of 2-chloromethylbenzaldehyde was 88.7% by weight. Yield: 87.3% (based on 2-chloromethylbenzalhalide).

Further, the oily product was mixed with 83.7 g of a 10 wt % aqueous disodium hydrogen phosphate solution, the resulting mixture was adjusted to a pH of 6 to 8, and liquid separation-treated, and 0.008 g of 2,6-bis(1,1-dimethylethyl)-4-methylphenol (BHT) (100 ppm relative to the oily product containing 2-chloromethylbenzaldehyde as a main component) was added.

A 500 mL flask was charged with 67.2 g (0.55 mol) of 2,5-dimethylphenol and 104.5 g (0.52 mol) of a 20 wt % aqueous sodium hydroxide solution, the temperature of the resulting mixture was elevated to 60° C., and the mixture was stirred at the same temperature for 3 hours. Another 500 mL flask was charged with 6.5 g (0.03 mol) of Aliquat (registered trademark) 175 and a total amount of the oily product containing 2-chloromethylbenzaldehyde as a main component. A mixture prepared from above 2,5-dimethylphenol and the 20 wt % aqueous sodium hydroxide solution was added dropwise thereto for 4 hours. The inner temperature of the flask content was retained at 45° C. until 3 hours of adding dropwise and, thereafter, the flask content was heated to 55° C. After completion of addition, the resulting mixture was stirred at 55° C. for 2 hours. The resulting reaction mixture was liquid separation-treated, and 130.0 g of a 10 wt % aqueous sodium dihydrogen phosphate solution was mixed into the oily layer. The resulting mixture was adjusted to a pH of 6 to 7, and liquid separation-treated to obtain 129.1 g of the crude product of 2-(2,5-dimethylphenoxymethyl)benzaldehyde. When the crude product was analyzed by a high-performance liquid chromatography internal standard method, a content of 2-(2,5-dimethylphenoxymethyl)benzaldehyde was 85.8% by weight. Yield: 83.8% (based on 1-dichrolomethyl-2-chloromethylbenzene)

Test Example 1

Stability Test of
2-(2,5-dimethylphenoxymethyl)benzaldehyde

Into a glass container was weighed 20 g of the oily product containing 2-(2,5-dimethylphenoxymethyl)benzaldehyde as a main component obtained in Example 1, the glass container was sealed, and allowed to stand in a constant temperature bath at 70° C., and the content of 2-(2,5-dimethylphenoxymethyl)benzaldehyde in the oily product was analyzed by a high-performance liquid chromatography internal standard method at every passage of the predetermined time. A content of 2-(2,5-dimethylphenoxymethyl)benzaldehyde in the oily product before allowing to stand in a constant temperature bath at 70° C. (before test), after 48 hours from allowing to stand, after 1 week from allowing to stand, and after 2 weeks from allowing to stand are shown in Table 1.

TABLE 1

| | Preservation term | | | |
|---|---|---|---|---|
| | Before test | After 48 hours | After 1 week | After 2 weeks |
| Content | 78.5% | 78.7% | 78.6% | 78.7% |

Test Example 2

Stability Test of
2-(2,5-dimethylphenoxymethyl)benzaldehyde

The reaction mixture containing 2-(2,5-dimethylphenoxymethyl)benzaldehyde as a main component, which was obtained by the same operation as that of Example 1, was liquid separation-treated, and the resulting oily layer was divided into three. From each of the oily layer which had been divided into three, an oily layer obtained by adjusting the mixture to a pH of 6 to 7 by washing using a 10 wt % aqueous sodium dihydrogen phosphate solution and liquid separation, an oily layer obtained by washing with a 5 wt % aqueous hydrochloric acid solution, performing liquid separation and, thereafter, further adjusting the mixture to a pH of 8 to 9 using an aqueous saturated sodium bicarbonate solution, and an untreated oily layer (aqueous layer before liquid separation pH 11) were obtained. Further, xylene was added at 30% by weight based on the weight of the resulting oily layer to obtain a uniform solution, which was preserved in a constant temperature bath at 70° C. A content of 2-(2,5-dimethylphenoxymethyl)benzaldehyde in a xylene solution of 2-(2,5-dimethylphenoxymethyl)benzaldehyde was analyzed by a high-performance liquid chromatography internal standard method at every passage of the predetermined time.

The analysis result is shown in Table 2. In the oily layer obtained by subjecting the reaction mixture containing 2-(2,5-dimethylphenoxymethyl)benzaldehyde as a main component to liquid separation treatment, and adjusting the mixture to a pH of 6 to 7 by washing, there was no reduction in the purity for 2 weeks, but in the oily layer obtained by liquid separation-treating the mixture having a pH of 8 to 9 and a pH of 11, reduction in the purity was progressively perceived.

TABLE 2

| pH | Before test | After 1 day | After 3 days | After 1 week | After 2 weeks | After 4 weeks | After 5 weeks |
|---|---|---|---|---|---|---|---|
| 6-7 | 58.3% | 58.4% | 58.3% | 58.8% | 58.4% | 57.5% | 57.1% |
| 8-9 | 58.1% | | 57.7% | 57.0% | — | — | — |
| 11 | 58.9% | 56.3% | 54.9% | 53.5% | — | — | — |

INDUSTRIAL APPLICABILITY

It is known that 2-(aryloxymethyl)benzaldehyde compounds such as 2-(2,5-dimethylphenoxymethyl)benzaldehyde are useful as an intermediate for producing agricultural germicides. The present invention can be industrially utilized as a new process for producing a 2-(aryloxymethyl)benzaldehyde compound and the like.

The invention claimed is:

1. A process for producing a 2-(aryloxymethyl)benzaldehyde compound represented by formula (4):

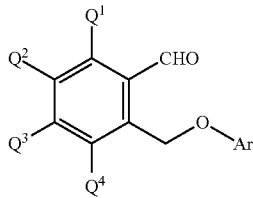
(4)

wherein $Q^1$, $Q^2$, $Q^3$ and $Q^4$ each represent independently a hydrogen atom or a halogen atom, and Ar represents a phenyl group optionally having a substituent, the process comprising step (A) of hydrolyzing a compound represented by formula (1):

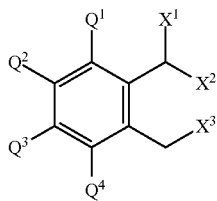
(1)

wherein $X^1$, $X^2$ and $X^3$ each represent independently a chlorine atom, a bromine atom or an iodine atom, and $Q^1$, $Q^2$, $Q^3$ and $Q^4$ are each as described above, and step (B) of reacting a compound represented by formula (2):

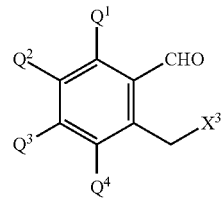
(2)

wherein $X^3$, $Q^1$, $Q^2$, $Q^3$ and $Q^4$ are each as described above, obtained in step (A), and a compound represented by formula (3):

Ar—OH   (3)

wherein Ar is as described above;
or a salt thereof.

2. The process according to claim 1, wherein step (A) is a step of hydrolyzing the compound represented by formula (1) in the presence of sulfuric acid.

3. The process according to claim 1, wherein step (A) is performed by mixing the compound represented by formula (1) and sulfuric acid having a concentration of 84.5% by weight or more, and further mixing the resulting mixture and water.

4. The process according to claim 1, wherein before step (B) is performed, the compound represented by formula (2) obtained in step (A) is neutralized.

5. The process according to claim 1, wherein before step (B) is performed, the compound represented by formula (2) obtained in step (A), and at least one selected from the group consisting of a polymerization inhibitor and an antioxidant are mixed.

6. The process according to claim 1, wherein step (B) is a step of reacting the compound represented by formula (2) obtained in step (A), and the compound represented by formula (3) or a salt thereof in the presence of a phase transfer catalyst.